(12) United States Patent
Essig et al.

(10) Patent No.: US 9,933,433 B2
(45) Date of Patent: Apr. 3, 2018

(54) ANTI-DRUG ANTIBODY ASSAY

(71) Applicant: Hoffmann-La Roche Inc., Nutley, NJ (US)

(72) Inventors: Ulrich Essig, Planegg (DE); Kay-Gunnar Stubenrauch, Penzberg (DE); Rudolf Vogel, Weilheim (DE); Uwe Wessels, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 288 days.

(21) Appl. No.: 14/452,122

(22) Filed: Aug. 5, 2014

(65) Prior Publication Data

US 2014/0349323 A1 Nov. 27, 2014

Related U.S. Application Data

(63) Continuation of application No. 12/440,504, filed as application No. PCT/EP2007/007803 on Sep. 7, 2007, now abandoned.

(30) Foreign Application Priority Data

Sep. 12, 2006 (EP) .................................. 06019016
Oct. 4, 2006 (EP) .................................. 06020797

(51) Int. Cl.
*G01N 33/68* (2006.01)
*C07K 16/42* (2006.01)
*C07K 16/06* (2006.01)

(52) U.S. Cl.
CPC ....... *G01N 33/6854* (2013.01); *C07K 16/065* (2013.01); *C07K 16/42* (2013.01); *C07K 16/4283* (2013.01); *C07K 2317/21* (2013.01); *C07K 2317/32* (2013.01); *C07K 2317/33* (2013.01); *C07K 2317/52* (2013.01)

(58) Field of Classification Search
CPC ................ G01N 33/6854; C07K 16/42; C07K 16/4283; C07K 2317/33; C07K 2317/52
See application file for complete search history.

(56) References Cited

U.S. PATENT DOCUMENTS

| 4,340,592 A * | 7/1982 | Adibi ...................... A23L 33/18 514/21.9 |
| 5,219,730 A | 6/1993 | Potocnjak et al. |
| 2003/0068664 A1 | 4/2003 | Albitar et al. |
| 2003/0092092 A1 | 5/2003 | Pandak et al. |
| 2003/0211103 A1 | 11/2003 | Buyse et al. |
| 2010/0041063 A1 * | 2/2010 | Essig ................... C07K 16/065 435/7.1 |

FOREIGN PATENT DOCUMENTS

| EP | 0580979 A2 | 2/1994 |
| WO | 96/20718 A2 | 7/1996 |
| WO | 2004/087756 A2 | 10/2004 |
| WO | 2004/096274 A1 | 11/2004 |
| WO | 2005/005635 A2 | 1/2005 |
| WO | 2005/018668 A1 | 3/2005 |
| WO | 2005/114218 A2 | 12/2005 |
| WO | 2006/066912 A2 | 6/2006 |
| WO | 2006/074076 A1 | 7/2007 |

OTHER PUBLICATIONS

Anonymous, "Secondary Antibodies Anti-Monkey," Internet Article, [Online], Feb. 2, 2005, pp. 1-4, XP002424585 Retrieved from the Internet: URL: http://www.researchd.com/rdiabs/2ndabmky.htm> [retrieved on Mar. 13, 2007].
Aslam M., and Dent, A., in "Bioconjugation", MacMillan Ref. Ltd. 1999, pp. 50-100.
Bourdage et al., "Effect of double antigen bridging immunoassay format on antigen coating concentration dependence and implications for designing immunogenicity assays for monoclonal antibodies," J. Pharm. Biomed. Anal. 39(3-4):685-690 (2005).
Bruck et al., "Purification of mouse monoclonal antibodies from ascitic fluid by DEAE Affi-Gel Blue chromatography," Methods Enzymol. 121:587-596 (1986).
Butler J.E: Solid phases in immunoassay. In: Immunoassay. Ed: Diamandis, E.P. & Christopoulos, T.K., Academic Press, San Diego 205-225 (1996).
Butler, "Solid supports in enzyme-linked immunosorbent assay and other solid-phase immunoassays," Methods 22 (1):4-23 (2000).
EPO Communication in Application No. 07802195.3, dated Aug. 31, 2012.
Hermanson G. T., "Bioconjugate Techniques Academic Press, San Diego." pp. 630-638 (1996).
Hoesel et al., "Development and evaluation of a new ELISA for the detection and quantification of antierythropoietin antibodies in human sera," J. Immunol. Methods 294(1-2):101-110 (2004) (Epub Oct. 4, 2004).
Levene et al., Journal of the Royal Society of MedicinE 98:145-152 (2005).
Martin et al., "Peer reviewed: nanomaterials in analytical chemistry," Anal. Chem. 70(9):322A-327A (1998).
Mihara et al., "Humanized antibody to human interleukin-6 receptor inhibits the development of collagen arthritis in cynomolgus monkeys," Clin. Immunol. 98(3):319-326 (2001).
Mire-Sluis et al., "Recommendations for the design and optimization of immunoassays used in the detection of host antibodies against biotechnology products," J. Immunol. Methods 289(1-2):1-16 (2004).
Nishimoto et al., "Humanized anti-interleukin-6 receptor antibody treatment of multicentric Castleman disease," Blood 106(8):2627-2632 (2005) (Epub Jul. 5, 2005).

(Continued)

*Primary Examiner* — Christine Foster
(74) *Attorney, Agent, or Firm* — Jones Day (57) ABSTRACT

The invention provides an antibody binding specifically to Cynomolgus IgG characterized by not binding to Human IgG, and a method for the immunological determination of an immune complex (DA/ADA complex) of a drug antibody (DA) and an antibody against said drug antibody (anti-drug antibody, ADA) in a sample of a monkey species using a double antigen bridging immunoassay.

5 Claims, 7 Drawing Sheets

(56) References Cited

OTHER PUBLICATIONS

Open Biosystems, "Product: Goat Anti-Monkey IgG (Gamma Specific) (product description)" Internet Article, [Online], p. 1, XP002424584 Retrieved from the Internet: URL: http://www.openbiosystems.com/collateral/antibodies/pi/catalog-antibodies/secondary-antibodies/Gt-A-Mn-IgG.pdf> [retrieved on Mar. 13, 2007].

Open Biosystems, "Secondary Antibodies—Goat Anti-Monkey" Internet Article, [Online], Aug. 13, 2004, pp. 1-6, XP002424583 Retrieved from the Internet: URL: http://web.archive.org/web/20040813233604/www.openbiosystems.com/secondary_antibodies_goat_anti_monkey.php> [retrieved on Mar. 13, 2007].

Pan et al., "Anti-idiotypic antibodies: biological function and structural studies," FASEB J. 9(1):43-49 (1995).

Shearer et al., "Serologic crossreactions among primate immunoglobulins," Dev. Comp. Immunol. 19(6):547-557 (1995).

Wadhwa et al., "Strategies for detection, measurement and characterization of unwanted antibodies induced by therapeutic biologicals," J. Immunol. Methods 278(1-2):1-17 (2003).

Wilchek et al., "Avidin-biotin mediated immunoassays: overview," Methods Enzymol. 184:467-469 (1990).

Abcam, Monkey IgG ELISA kit (ab190549) two site enzyme linked immunoassay (Protocol Booklet and Datasheet), dated Oct. 10, 2014 (27 pages total).

* cited by examiner

ANTI-DRUG ANTIBODY ASSAY

This application claims priority to and is a continuation of pending U.S. patent application Ser. No. 12/440,504, filed Mar. 9, 2009, which in turn is a National Stage of International Application No. PCT/EP2007/007803, filed Sep. 7, 2007, which claims the benefit of European Patent Application No. 06019016.2, filed Sep. 9, 2006. Each of these applications is hereby incorporated by reference herein in its entirety.

The invention comprises a method for the determination of anti-drug antibodies and kits for the use of such assays.

BACKGROUND OF THE INVENTION

Standard solid-phase immunoassays with monoclonal antibodies involve the formation of a complex between an antibody adsorbed on a solid phase (capture antibody), an antigen, and an antibody to another epitope of the antigen conjugated with an enzyme or a detectable label (tracer antibody). Thus, a sandwich is formed: solid phase-capture antibody-antigen-tracer antibody. In the sandwich, the activity of the antibody-conjugated enzyme (or the amount of the detectable label) is proportional to the antigen concentration in the incubation medium. One sandwich assay is the double antigen bridging immunoassay whereby capture and tracer antibodies bind to different epitopes of the antigen. Hoesel, W., et al., in J. Immunol. Methods 294 (2004) 101-110, report an anti-EPO double antigen bridging assay whereby a mixture of immobilized rhEPO coupled to amino groups and to carbohydrate groups was used. Immunoassays such as the double antigen bridging ELISA are common assay types in the investigation of an immunogenic answer of a patient to an antibody drug. Mire-Sluis, A. R., et al., in J. Immunol. Methods 289 (2004) 1-16, summarize the recommendations for the design and optimization of immunoassays using detection of host antibodies against biotechnology products. According to Mire-Sluis et al., the well-known anti-drug antibody assay formats show considerable disadvantages. Anti-drug antibody assays are mentioned, for example, in WO 2005/045058 and WO 90/006515. Anti-idiotypic antibody assays are mentioned, for example, in U.S. Pat. No. 5,219,730, WO 87/002778, EP 0 139 389, and EP 0 170 302. Wadhwa, M., et al., in J. Immunol. Methods 278 (2003) 1-17, report strategies for the detection, measurement and characterization of unwanted antibodies induced by therapeutic biologicals. An immunological assay for the immunological determination of an antibody against a drug antibody in a sample using a double antigen bridging immunoassay is described in PCT/EP2007/001935. An immunological assay for the determination of human antibodies in monkeys is described in WO 2006/066912. In the art (e.g. US 2003/0068664) also assay systems are known, which allow for the detection of active therapeutic antibodies. Such systems require the binding of the antigen to a solid phase, binding of the therapeutic antibody to this bound antigen and detection of the therapeutic antibody bound via the antigen to the solid phase.

SUMMARY OF THE INVENTION

The invention provides an antibody which binds specifically to Cynomolgus IgG and does not bind to Human IgG. Preferably the antibody is a monoclonal antibody.

In a preferred embodiment the antibody according to the invention is produced by the cell line 3.25.12 (DSM ACC2799), 3.29.15 (DSM ACC2800), 4.38.30 (DSM ACC2801), 7.57.41 (DSM ACC2802), or 7.72.32 (DSM ACC2803).

The invention provides a method for the immunological determination of an immune complex of a drug antibody (DA) and an antibody against said drug antibody (anti-drug antibody, ADA) in a sample of a monkey species using a sandwich assay, i.e. a double antigen bridging immunoassay.

The immune complex is further abbreviated as DA/ADA complex.

The invention provides a method for the immunological determination of a DA/ADA complex in a sample using a sandwich type or double antigen bridging immunoassay comprising a capture antibody and a tracer antibody, characterized in that one of said antibodies, i.e. either the tracer antibody or the capture antibody, is an antibody specifically binding to Cynomolgus IgG and the other antibody is an antibody specifically binding to Human immunoglobulin.

In a preferred embodiment of the invention, the capture antibody is an anti-Human Ig antibody specifically binding to human immuno globulin, and the tracer antibody is an anti-Cynomolgus IgG antibody specifically binding to Cynomolgus IgG. In a preferred embodiment of the invention, the capture antibody is an anti-Cynomolgus IgG antibody specifically binding to Cynomolgus IgG, and the tracer antibody is an anti-Human Ig antibody specifically binding to Human Ig.

Preferably the anti-Human Ig antibody is specifically binding to Human IgG. Preferably the anti-Cynomolgus IgG antibody and/or the anti-Human Ig antibody is/are monoclonal. Preferably said antibody specifically binding Human immunoglobulin is not binding to Cynomolgus IgG. Preferably said antibody binding to Human immunoglobulin is produced by the cell line DSM ACC2708.

Preferably said antibody binding to Cynomolgus IgG is not binding to Human IgG. Preferably said antibody binding to Cynomolgus IgG is produced by the cell line 3.25.12 (DSM ACC2799), 3.29.15 (DSM ACC2800), 4.38.30 (DSM ACC2801), 7.57.41 (DSM ACC2802), or 7.72.32 (DSM ACC2803).

In the course of said determination a complex is formed between anti-Cynomolgus IgG antibody, DA/ADA complex, and anti-Human Ig antibody and the amount of the complex formed is correlated to the concentration of the DA/ADA complex, DA and/or ADA.

According to the invention a direct sample analysis for detection of formed DA/ADA complex can be performed. In such an assay positive signals are only found if the sample contains both drug antibodies and anti-drug antibodies.

According to the invention alternatively a sample analysis after pre-incubation with a predetermined amount of the drug antibody is (can be) performed. In such an assay positive signals are found if the sample contains anti-drug antibodies independent of the presence/absence of drug antibodies in the sample.

Preferably the capture antibody is conjugated to the solid phase by passive adsorption and therefore conjugated to the solid phase at at least two different antibody sites. Passive adsorption is, e.g., described by Butler, J. E., Solid Phases in Immunoassay, In: Immunoassays, Diamandis, E. P. and Christopoulos, T. K. (eds.) Academic Press San Diego (1996), pp. 205-225.

In a preferred embodiment of the invention, the capture antibody is immobilized via a specific binding pair. Such a binding pair (first component/second component) is, for example, Streptavidin or Avidin/biotin, antibody/antigen (see, for example, Hermanson, G. T., et al., Bioconjugate Techniques, Academic Press, 1996), lectin/polysaccharide, steroid/steroid binding protein, hormone/hormone receptor, enzyme/substrate, IgG/Protein A and/or G, etc. Preferably, the capture antibody is conjugated to biotin and immobilization is performed via immobilized Avidin or Streptavidin.

Preferably conjugation of the antibody to its conjugation partner is performed by chemically binding via N-terminal and/or ε-amino groups (lysine), ε-amino groups of different lysines, carboxy-, sulfhydryl-, hydroxyl- and/or phenolic functional groups of the amino acid backbone of the antibody and/or sugar alcohol groups of the carbohydrate structure of the antibody.

In a preferred embodiment of the invention, the tracer antibody is conjugated to a detectable label, preferably conjugated via a specific binding pair. Such a binding pair (first component/second component) is, for example, Streptavidin or Avidin/biotin, antibody/antigen, lectin/polysaccharide, steroid/steroid binding protein, hormone/hormone receptor, enzyme/substrate, IgG/Protein A and/or G, etc. Preferably, the tracer antibody is conjugated via digoxigenin and an antibody against digoxigenin to the detectable label. Alternatively the tracer antibody is conjugated to an electrochemiluminescent label, like a ruthenium bispyridyl complex.

In a further embodiment the invention provides a method for the immunological determination of an antibody against a drug antibody (anti-drug antibody, ADA) in a sample of a monkey species using a sandwich type or double antigen bridging immunoassay.

The invention provides a method for the immunological determination of an ADA in a sample using a sandwich type or double antigen bridging immunoassay comprising a capture antibody and a tracer antibody, characterized in that one of said antibodies is an antibody specifically binding to Cynomolgus IgG and which does not bind to Human IgG and the other antibody is a drug antibody.

In a preferred embodiment of the immunological determination of an ADA, the capture antibody is a drug antibody and the tracer antibody is an anti-Cynomolgus IgG antibody specifically binding to Cynomolgus IgG and not binding to Human IgG. In a further preferred embodiment of the immunological determination of an ADA, the capture antibody is an anti-Cynomolgus IgG antibody specifically binding to Cynomolgus IgG and not binding to Human IgG and the tracer antibody is a drug antibody. In the course of said determination a complex is formed between drug antibody, ADA, and anti-Cynomolgus IgG antibody and the amount of said complex formed is correlated to the concentration of the ADA. In a preferred embodiment of the immunological determination of an ADA, the anti-Cynomolgus IgG antibody is a monoclonal antibody (anti-Cynomolgus mAb).

Another embodiment of the invention are the hybridoma cell lines 3.25.12 (DSM ACC2799), 3.29.15 (DSM ACC2800), 4.38.30 (DSM ACC2801), 7.57.41 (DSM ACC2802), 7.72.32 (DSM ACC2803).

Another aspect of the invention is an antibody composition for use in a method according to the invention comprising a mixture of the antibody produced by the cell line DSM ACC2799, the cell line DSM ACC2800, the cell line DSM ACC2801, the cell line DSM ACC 2802, and/or the cell line DSM ACC2803.

DETAILED DESCRIPTION OF THE INVENTION

The current invention provides an antibody which binds specifically to Cynomolgus IgG and does not bind to Human IgG.

The term "drug antibody" according to the invention denotes an antibody which can be administered to an individual for the treatment of a disease. Within one assay performed according to the invention, the drug antibody and the capture antibody, or the drug antibody and the tracer antibody, respectively, comprise the "same" antibody molecule, e.g. recombinantly produced with the same expression vector and comprising the same amino acid sequence. Drug antibodies (therapeutic monoclonal antibodies) are being used widely for the treatment of various diseases such as oncological diseases (e.g. hematological and solid malignancies including non-Hodgkin's lymphoma, breast cancer, and colorectal cancer), immunological diseases, central nervous diseases, vascular diseases, or infectious diseases. Such antibodies are described, for example, by Levene, A. P., et al., Journal of the Royal Society of Medicine 98 (2005) 145-152. Such antibodies are, for instance, antibodies against CD20, CD22, HLA-DR, CD33, CD52, EGFR, G250, GD3, HER2, PSMA, CD56, VEGF, VEGF2, CEA, Levis Y antigen, IL-6 receptor, or IGF-1 receptor. Therapeutic antibodies are also described by Groner, B., et al., Curr. Mol. Meth. 4 (2004) 539-547; Harris, M., Lancet Oncol. 5 (2004) 292-302.

An example (preferably monoclonal) therapeutic/drug antibody is an antibody against IL-6 receptor (mAb IL-6R). Such an antibody is for example described by Mihara, M., et al., Clin. Immunol. 98 (2001) 319-326; Nishimoto, N., et al., Blood 106 (2005) 2627-2632; in clinical trial NCT00046774; in WO 2004/096274.

An example (preferably monoclonal) therapeutic/drug antibody is an antibody against IGF-1 receptor (mAb IGF-1R). Such an antibody is for example described in WO 2004/087756, WO 2005/005635.

"Anti-drug antibodies" are antibodies, which may be directed against any region of the drug antibody, like e.g. the variable domain, the constant domains, or the glycostructure of the drug antibody. Such anti-drug antibodies may occur during antibody therapy as an immunogenic reaction of a patient (see Pan, Y., et al., FASEB J. 9 (1995) 43-49). Most of the "anti-drug antibodies" bind to one or more of the complementary determining regions of the drug antibody. The affinity of anti-drug antibodies to their drug antibody's antigen is in general lower compared to the affinity of the drug antibody for its target antigen.

An "anti-Cynomolgus IgG antibody" is an antibody, preferably monoclonal (i.e. a monoclonal anti-Cynomolgus antibody, mAb<Cyno IgG>), specifically binding to Cynomolgus IgG (Cynomolgus immunoglobulin G). Such an antibody will bind to a Cynomolgus IgG with a dissociation constant (=KDiss.) of at least $10^{-9}$ mol/L, more preferred with a KDiss. of at least $10^{-10}$ mol/L. At the same time the property of not binding to Human IgG is insured by a KDiss. of $10^{-8}$ mol/L or worse, e.g. of $10^{-5}$ mol/L. Also preferred, the antibody binding to Cynomolgus IgG and not binding to Human IgG will have a KDiss.-gap of at least 100-fold between its reactivity towards Cynomolgus IgG and towards Human IgG, respectively.

Preferably the anti-Cynomolgus IgG antibody binds also Marmoset IgG, Rhesus IgG, and Baboon IgG with a dissociation constant (=KDiss.) of at least $10^{-8}$ mol/l, preferred of $10^{-9}$ mol/L, more preferred with a KDiss. of at least $10^{-10}$ mol/L.

In one embodiment the antibody according to the invention is a monoclonal antibody. The term "monoclonal" as used within the current application denotes a population of antibodies produced by a single cell or its progeny and also binding to a single antigenic determinant of its target antigen. The term "not binding to Human IgG" or grammatical equivalents thereof as used within this application denotes an antibody that shows no specific binding to a Human IgG, i.e. which has a KDiss. of $10^{-7}$ mol/L or worse, e.g. of $10^{-5}$ mol/L. This does not include a polyclonal population of Cynomolgus antibodies which have been cross-adsorbed to human immunoglobulins in order to remove Cynomolgus IgG binding to Human IgG. The cross-adsorption does not provide for a population of polyclonal antibodies, let alone monoclonal antibodies, that do not bind to human IgG due to the binding equilibrium formed in this process. Due to this equilibrium is a number of antibodies binding to Human IgG not cross-adsorbed and remains in solution and, thus, in the obtained antibody preparation. Thus, immunoglobulins once cross-adsorbed to Human IgG will not completely be depleted of any anti-Human IgG binding and still show Human IgG binding.

Further aspects of the current invention are the cell line DSM ACC2799, the cell line DSM ACC2800, the cell line DSM ACC2801, the cell line DSM ACC 2802, the cell line DSM ACC2803, as well as the monoclonal antibody produced by the cell line DSM ACC2799, or the cell line DSM ACC2800, or the cell line DSM ACC2801, or the cell line DSM ACC 2802, or the cell line DSM ACC2803. Another aspect of the current invention is an antibody composition comprising a mixture of the antibody produced by the cell line DSM ACC2799, the cell line DSM ACC2800, the cell line DSM ACC2801, the cell line DSM ACC 2802, and/or the cell line DSM ACC2803. The current invention further comprises a composition comprising an antibody produced by the cell line DSM ACC2799, or the cell line DSM ACC2800, or the cell line DSM ACC2801, or the cell line DSM ACC 2802, or the cell line DSM ACC2803.

With the antibody according to the current invention the background variation of individual Human sera can be minimized or even excluded.

The term "monkey" according to the invention means Cynomolgus, Marmoset, Rhesus, and Baboon. Preferably denotes "monkey" Cynomolgus, Rhesus Macaque, and Baboon Preferably the anti-Human Ig antibody (Ig denotes immunoglobulin) is an antibody specifically binding to an epitope which is not present on the immunoglobulin of cynomolgae as described in WO 2006/066912. This epitope is characterized by its binding to MAB<H-Fcγ pan>M-R10Z8E9, also denoted MAB<h-Fc gamma>M-R10Z8E9, or briefly MAB M-R10Z8E9. In a preferred embodiment according to the present invention, the anti-Human Ig antibody is further characterized by binding to the same epitope as MAB M-R10Z8E9. MAB M-R10Z8E9 is produced by the cell line deposited with DSMZ on Dec. 22, 2004, as DSM ACC2708. Preferably the anti-Human Ig antibody comprises the variable heavy and light chain domains of MAB M-R10Z8E9. More preferably the anti-Human Ig antibody comprises the CDR regions of the variable heavy and light chain domains of MAB M-R10Z8E9 and a non-human framework. Preferably the anti-Human Ig antibody is a monoclonal antibody (anti-Human Ig mAb).

The binding properties of an antibody, especially the KDiss., are preferably assessed by a BIAcore® instrument. In this method binding properties are evaluated by changes in surface plasmon resonance (SPR). It is convenient to bind the antibody under investigation to the solid phase (called chip) and to assess binding of a monoclonal antibody, a polyclonal antibody, or even of serum comprising IgG to this coated chip.

Solid supports for the immunoassays according to the invention are widely described in the state of the art (see, e.g., Butler, J. E., Methods 22 (2000) 4-23).

The principles of different immunoassays are described, for example, by Hage, D. S., in Anal. Chem. 71 (1999) 294R-304R. Lu, B., et al., in Analyst. 121 (1996) 29R-32R, report the orientated immobilization of antibodies for the use in immunoassays. Avidin-biotin-mediated immunoassays are reported, for example, by Wilchek, M. and Bayer, E. A., Methods Enzymol. 184 (1990) 467-469.

The term "double antigen bridging immunoassay" as used within the current invention denotes a sandwich type immunoassay in which the antigen is bound by two different antibodies each binding to a different not overlapping or interfering epitope of the antigen. In this assay a sandwich comprising a capture antibody, the antigen, and a tracer antibody is formed and, thus, the antigen bridges two antibodies binding to it.

Monoclonal antibodies and their constant domains contain as proteins a number of reactive side chains for coupling to a binding partner like a surface, a protein, a polymer (e.g. PEG), cellulose, or polystyrene, an enzyme, or a member of a binding pair. Chemical reactive groups of antibodies are, for example, amino groups (ϵ-amino groups of lysines, alpha-amino groups), thiol groups (cystines, cysteines, methionines), carboxylic acid groups (aspartic acids, glutamic acids), and sugar-alcohol groups. Such methods are described, e.g., by Aslam, M. and Dent, A., Bioconjuation, MacMillan Ref. Ltd. (1999), pp. 50-100.

The term "sample" includes any quantity of a substance from a monkey. Such substances include, but are not limited to, whole blood, serum, or plasma from such an individual, which are the most widely used sources of sample in preclinical routine.

The term "solid phase" means a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; cuvettes, tubes, or other spectrometer sample containers. A solid phase component of an assay is distinguished from inert solid surfaces with which the assay may be in contact in that a "solid phase" contains at least one moiety on its surface, which is intended to interact with the capture antibody. A solid phase may be a stationary component, such as a tube, strip, cuvette, or microtiter plate, or may be a non-stationary component, such as beads and microparticles. Microparticles can also be used as a solid phase for homogeneous assay formats. A variety of microparticles that allow either non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry-News & Features 70 (1998) 322A-327A, which is incorporated herein by reference.

Chromogens (fluorescent or luminescent groups and dyes), enzymes, NMR-active groups or metal particles, haptens, such as, e.g., digoxigenin, are examples of detectable labels. The detectable label can also be a photoactivatable crosslinking group, e.g. an azido or an azirine group. Metal chelates which can be detected by electrochemoluminescence are also preferred signal-emitting groups, with particular preference being given to ruthenium chelates, e.g. a ruthenium (bispyridyl)$_3^{2+}$ chelate. Suitable ruthenium labeling groups are described, for example, in EP 0 580 979, WO 90/05301, WO 90/11511, and WO 92/14138.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates, In: Practice and theory of enzyme immunoassays, Burdon, R. H. and v. Knippenberg, P. H. (eds.), Elsevier, Amsterdam (1990) pp. 221-278, and various volumes of Colowick, S. P. and Caplan, N. O. (eds.), "Methods in Enzymology", Academic Press, dealing with immunological detection methods, especially volumes 70, 73, 74, 84, 92, and 121.

Antibodies according to the invention can be produced by the hybridoma cell lines 3.25.12 (DSM ACC2799), 3.29.15 (DSM ACC2800), 4.38.30 (DSM ACC2801), 7.57.41 (DSM ACC2802), 7.72.32 (DSM ACC2803), which also by itself are an aspect of the current invention. Further antibodies according to the invention, i.e. specifically binding to Cynomolgus IgG and not binding to Human IgG, can be found, for example using the method outlined in Example 3.

Alternatively, for example, a method can be used in which in a first step epitope overlapping of two antibodies binding to the same target antigen is determined with the help of a competitive test system. For this purpose, for example with the help of an enzyme immunoassay, there is tested the extent to which the antibody in question competes with the known antibody for the binding to an immobilized target antigen, e.g. an antibody produced by the cell lines according to the invention. For this purpose, an appropriately immobilized target antigen is incubated with the known antibody in labeled form and an excess of the antibody in question. By determining the amount of the bound antibody in labeled form in the presence and absence of the antibody in question can the extent to which the antibody in question can displace the known antibody from binding be evaluated. If there is a displacement of more than 20%, preferably of more than 30%, at the same concentration or a displacement of more than 70%, preferably of more than 80%, at higher concentrations, preferably in the case of $10^3$-$10^5$-fold excess of the antibody in question, referred to the known antibody, epitope overlapping is occurring and both antibodies bind to the same or an overlapping part of the same epitope. Such an identified antibody is used in the second step of the method. Herein the binding of the antibody identified in step one to Human IgG is determined. Such a determination can be performed, e.g. with an ELISA, an immunoassay, or with surface plasmon resonance. If no binding to Human IgG can be determined, such an antibody is defined as an antibodies specifically binding to Cynomolgus IgG and not binding to Human IgG. Alternatively an antibody according to the invention can be identified by determining the KDiss. towards Cynomolgus IgG and Human IgG separately and comparing these values.

The current invention reports an immunological determination method for the determination of complexes of drug antibodies and anti-drug antibodies, which are in the following denoted as DA/ADA complexes. In more detail the current invention comprises a method for the immunological determination of an immune complex (DA/ADA complex) of a drug antibody (DA) and an antibody against said drug antibody (anti-drug antibody, ADA) in a sample of a monkey species using a sandwich type immunoassay, comprising a capture antibody and a tracer antibody, wherein one of said antibodies is an antibody specifically binding to Cynomolgus IgG and preferably is not binding to Human IgG, and the other of said antibodies is an antibody specifically binding to Human IgG and preferably is not binding to Cynomolgus IgG. In one embodiment is the capture antibody an antibody specifically binding to Human IgG and not binding to Cynomolgus IgG and the tracer antibody is an antibody specifically binding to Cynomolgus IgG and not binding to Human IgG. In a different embodiment is the capture antibody an antibody specifically binding to Cynomolgus IgG and not binding to Human IgG and the tracer antibody is an antibody specifically binding to Human IgG and not binding to Cynomolgus IgG. Another embodiment of the current invention is that the antibody specifically binding to Cynomolgus IgG and/or the antibody specifically binding to Human IgG is/are monoclonal.

In a preferred embodiment of the current method is the sample preincubated with a predetermined amount of the drug antibody. This allows for the detection of anti-drug antibodies irrespectably of the presence of the drug antibody in the sample, as the current method is for the detection of DA/ADA-complexes (see e.g. FIGS. 5 and 6).

According to the high identity between Human or humanized drug antibodies and Cynomolgus IgGs are the main antigenic determinants of the drug antibody its complementary determining regions. These antigenic determinants are preferably recognized by the anti-drug antibody. Thus, the majority of anti-drug antibodies recognizes and, therefore, binds to the complementary determining regions of the corresponding drug antibody. The formation of the anti-drug antibody-drug antibody complex masks the antigenic epitopes and, thus, competes with the determination of said complex in a sandwich assay.

The anti-Human IgG antibody is an antibody specifically binding to an epitope which is not present on the immunoglobulins obtained from a cynomolgus as e.g. described in WO 2006/066912. In a preferred embodiment is the anti-Human IgG antibody further characterized by binding to the same epitope as the antibody produced by the cell line DSM ACC 2708, which is binding to a epitope that is present on all subclasses of human immunoglobulin of class G and appears not to be present on the immunoglobulin of most experimental animals except on the IgG of chimpanzees. In a further preferred embodiment is the anti-Human IgG antibody the antibody produced by cell line DSM ACC2708.

It has been surprisingly found that with the method according to the invention an incomplete detection of anti-drug antibody is prevented. If e.g. the capture molecule binds to the same antigenic determinant as the anti-drug antibody, i.e. the CDRs of the drug antibody, the binding of the drug antibody to the capture molecule would block these epitopes, i.e. mask them for the anti-drug antibody, and thus prevent the anti-drug antibody from binding and being detected. This results in an incomplete detection of anti-drug antibodies in the sample. The anti-drug antibody normally has a low binding affinity towards the drug antibody, therefore requiring the cooperation of both antigen binding regions of the anti-drug antibody for the binding of the drug antibody. Thus, no binding to the capture molecule is possible leading also to a low detection of the anti-drug antibody. Therefore, the capture via the CDRs of an anti-drug antibody is not suited for an assay.

Thus, one aspect of the current invention is a method for the immunological determination of an immune complex (DA/ADA complex) of a drug antibody (DA) and an antibody against said drug antibody (anti-drug antibody, ADA) in a sample of a monkey species using a sandwich immunoassay, comprising a capture antibody and a tracer antibody, wherein one of said antibodies is an antibody specifically binding to Cynomolgus IgG and not binding to Human IgG, and the other antibody is an antibody specifically binding to Human IgG and not binding to Cynomolgus IgG. In one embodiment of this aspect is the antibody specifically binding to Cynomolgus IgG and not binding to Human IgG produced by the cell line DSM ACC2799 or DSM ACC2800 or DSM ACC2801 or DSM ACC2802 or DSM ACC2803. In another embodiment of this aspect is the antibody specifically binding to Human IgG and not binding to Cynomolgus IgG produced by the cell line DSM ACC2708.

In one embodiment of the current method is the amount of complex formed correlated to the concentration of DA/ADA complex, DA, and/or ADA.

In another embodiment is the capture antibody binding the anti-drug antibody or the DA/ADA complex not binding to the CDRs or the framework region in close sequential or geometric proximity of the CDRs of the anti-drug antibody.

Another aspect of the current invention is a method for the immunological determination of an antibody against a drug antibody (anti-drug antibody, ADA) in a sample of a monkey species using a sandwich immunoassay comprising a capture antibody and a tracer antibody, wherein the capture antibody is an antibody specifically binding to Cynomolgus IgG and not binding to Human IgG and the tracer antibody is a drug antibody. Also an aspect is a method for the immunological determination of an antibody against a drug antibody (anti-drug antibody, ADA) in a sample of a monkey species using a sandwich immunoassay comprising a capture antibody and a tracer antibody, wherein the tracer antibody is an antibody specifically binding to Cynomolgus IgG and not binding to Human IgG and the capture antibody is the drug antibody.

The preferred hybridoma cell lines according to the invention, 3.25.12, 3.29.15, 4.38.30, 7.57.41, and 7.72.32 were deposited, under the Budapest Treaty on the international recognition of the deposit of microorganisms for the purposes of patent procedure, with Deutsche Sammlung von Mikroorganismen and Zellkulturen GmbH (DSMZ), Mascheroder Weg 1B, D-38124 Braunschweig, Germany:

| Clone | Deposition No. | Date of Deposit |
|---|---|---|
| 3.25.12 | DSM ACC2799 | 24 Aug. 2006 |
| 3.29.15 | DSM ACC2800 | 24 Aug. 2006 |
| 4.38.30 | DSM ACC2801 | 24 Aug. 2006 |
| 7.57.41 | DSM ACC2802 | 24 Aug. 2006 |
| 7.72.32 | DSM ACC2803 | 24 Aug. 2006 |
| MAB M-R10Z8E9 | DSM ACC2708 | 22 Dec. 2004 |

The antibodies obtainable from said cell lines are embodiments of the current invention.

The following examples and figures are provided to aid the understanding of the present invention, the true scope of which is set forth in the appended claims. It is understood that modifications can be made in the procedures set forth without departing from the spirit of the invention.

DESCRIPTION OF FIGURES

FIG. 1: Assay for Detection of DA/ADA complexes—without adding DA.
Biotinylated anti-Human Ig antibodies are immobilized to a Streptavidin-coated microtiter plate (SA-MTP). Drug antibody/anti-drug antibody (DA/ADA) complexes are captured by the immobilized anti-Human Ig antibodies (Bi; biotinylated). The bound DA/ADA complex is detected by digoxigenin-labeled (Dig; digoxinylated) anti-Cynomolgus IgG antibodies and anti-digoxigenin antibody horse-radish peroxidase (POD) conjugate pAb<Dig>POD). Human IgG chemically conjugated to Cynomolgus IgG is used as standard.

FIG. 2: Assay for Detection of DA/ADA complexes—with adding DA.
Before sample analysis monkey serum samples were diluted in PBS-based buffer and spiked with drug antibody. After 15 min. preincubation the samples were analyzed with above-mentioned ELISA (see description of FIG. 1).

FIG. 3: Assay for Detection of ADA using anti-Cynomolgus antibodies.
The biotinylated drug antibody is bound to a Streptavidin-coated microtiter plate (SA-MTP) (Bi; biotinylated). The anti-drug antibody (ADA) binds the immobilized drug antibody. The bound ADA is detected by digoxigenin-labeled (Dig; digoxinylated) anti-Cynomolgus IgG antibodies and anti-digoxigenin antibody horse-radish peroxidase conjugate (pAb<Dig>POD). Anti-Human IgG antibody chemically conjugated to Cynomolgus IgG is used as standard.

FIG. 4: Standard curve of the DA/ADA complex assay.
The optical densities (ODs) are given for various concentrations of human IgG chemically conjugated to Cynomolgus IgG diluted in PBS-based-buffer with 1% (v/v) Cynomolgus serum.

EXAMPLES

Example 1

Preparation of Cynomolgus IgG and Cynomolgus Fc fragment
a) Preparation of Cynomolgus IgG
The cynomolgus serum has been delipidated with Aerosil® 380 and precipitated with ammonium sulfate (ad 2.0 M). The pellet was homogenized in phosphate buffer and dialyzed against phosphate buffer, pH 7.0. The mixture was separated by DEAE ion exchange chromatography at pH 7.0 and the IgG in the flow through was concentrated and purified by gel filtration.

b) Preparation of Cynomolgus Fc

The purified IgG of a) was fragmentized with papain (4 mU papain per mg IgG) in the presence of 15 mM cysteine at 37° C. at pH 7.0. After 80 min. the mixture was incubated with iodoacetamide (ad 30 mM) at 25° C. and dialyzed afterwards against 10 mM HEPES buffer, with 30 mM NaCl, pH 7.5. The mixture was separated by Q-Sepharose ion exchange chromatography. The Fab fraction was in the flow through and the Fc fraction was eluted by using a salt gradient up to 1 M sodium chloride. Finally the Fc fraction was dialyzed against phosphate buffer and purified by gel filtration.

Example 2

Generation of Monoclonal Anti-Cynomolgus IgG Antibodies a) Immunization of Mice

Female Balb/c or NMRI mice, respectively, 8-12 weeks of age, were primarily immunized intraperitoneally with 100 µg of Cynomolgus IgG (Cynomolgus immunoglobulin G) or Cynomolgus Fc mixed with CFA (Complete Freund's Adjuvant). Three further intraperitoneal immunization steps followed after 4, 7, and 10 weeks, with application of 100 µg of Cynomolgus IgG per mouse mixed with IFA (Incomplete Freund's Adjuvant). Subsequently, intravenous boost immunizations were done, each with 100 µg of Cynomolgus IgG in PBS (phosphate buffered saline; antihistamine and adrenaline added) 3 days before the fusion.

b) Fusion and Cloning

Fusion of the spleen cells of the mice immunized according to a) with myeloma cells was performed according to Galfré, G. and Milstein, C., Methods Enzymol. 73 (1981) 3-46. Approximately $1 \times 10^8$ splenocytes were mixed with approximately $2 \times 10^7$ myeloma cells (P3x63-Ag8.653, ATCC CRL1580) and centrifuged (10 min. at 300×g and 4° C.). The cells were washed afterwards once with the culture medium RPMI 1640 without FCS (fetal calf serum), and centrifuged again at 400×g in a 50 mL pointed vial. Thereafter, 1 mL of PEG (polyethylene glycol, molecular weight 4,000 g/mol) was added, mixing was carried out by the pipetting. After 1 min. in a water bath at 37° C., 5 mL of RPMI 1640 without FCS were added drop wise, the suspension was mixed, filled up to 50 mL with RPMI 1640 with 10% (v/v) FCS, and then centrifuged. The sedimented cells were resuspended in RPMI 1640 with 10% FCS, and plated in hypoxanthine-azaserine selection medium (100 mmol/L hypoxanthine, 1 µg/mL azaserine in RPMI 1640 with 10% PCS) containing the growth factor Interleukin 6 (IL-6, 100 U/mL). After approximately 10 days, the primary cultures were assayed for specific antibody synthesis (cf. Example 3). Primary cultures exhibiting binding to Cynomolgus IgG as well as no cross reaction with Human normal IgG were individualized by single cell deposition into 96-well cell culture plates using a flow cytometer (FACSAria, BD Biosciences), the medium contained the growth factor Interleukin 6 (100 U/mL). By following this protocol, the deposited clones (Table 1) were generated. Cell lines useful in the current invention were deposited with Deutsche Sammlung von Mikroorganismen and Zellkulturen GmbH (DSMZ), Mascheroder Weg 1B, D-38124 Braunschweig, Germany (Table 1).

TABLE 1

Anti-Cynomolgus mAb clones

| Clone | IgG Class and Subclass | Immunogen | Deposition No. | Date of Deposit |
|---|---|---|---|---|
| 3.25.12 | IgG1, kappa | IgG | DSM ACC2799 | 24 Aug. 2006 |
| 3.29.15 | IgG1, kappa | IgG | DSM ACC2800 | 24 Aug. 2006 |
| 4.38.30 | IgG1, kappa | IgG | DSM ACC2801 | 24 Aug. 2006 |
| 7.57.41 | IgG2a, kappa | Fc | DSM ACC2802 | 24 Aug. 2006 |
| 7.72.32 | IgG1, kappa | Fc | DSM ACC2803 | 24 Aug. 2006 | c) Production of Immunoglobulin from the Cell Culture Supernatants

The generated hybridoma cell lines were inoculated at initial cell densities (live cells) between $1.0 \times 10^5$ and $2.2 \times 10^5$ cells per mL (depending on the individual cell line) in RPMI 1640 medium supplemented with 10% FCS, and expanded in a spinner technology for a period of 9 to 16 days (depending on the individual cell line). In the harvested culture supernatants, concentrations between 36 and 61 µg of monoclonal antibody per mL were achieved. Purification of the antibodies from the culture supernatants was done according to standard protein chemical methods, e.g. according to Bruck, C., et al., Methods Enzymol. 121 (1986) 587-596.

Example 3

Screening Assays for Detection of Anti-Cynomolgus IgG Antibodies a) Primary Screening for Antibodies Binding Preferentially to Cynomolgus IgG For the determination of the specificity of the antibodies in the culture supernatants of the hybridoma cells, MTPs (microtiter plates) pre-coated with recombinant Streptavidin (MicroCoat, Bernried, lot MC 1098) were coated with biotinylated Cynomolgus IgG, 250 ng/mL, or biotinylated Human IgG, 250 ng/mL, respectively, in PBS supplemented with 1.0% (w/v) BSA II (100 µL per well, 60 min. incubation at ambient temperature, with shaking), and subsequently washed 3 times with 0.9% (w/v) NaCl/0.05% Tween® 20. In the next step, per well 100 µL of the antibody solution to be assayed (culture supernatant) were added, and incubated for 60 min. at ambient temperature, with shaking. After 3 wash steps with 0.9% (w/v) NaCl/0.05% Tween® 20 per well, 100 µL of a horseradish peroxidase-labeled F(ab')$_2$ fragment of a polyclonal sheep anti-mouse Fcγ antibody were added for the detection of bound sample antibody, and incubated for 60 min. at ambient temperature, with shaking. Subsequently, washing was performed as above. Finally, per well 100 µL of ABTS® (Roche Diagnostics GmbH, catalog no. 1684302) were added. After 30 min. incubation at ambient temperature, the extinction (OD) was measured at 405 and 492 nm [405/492] in a commercial microtiter plate ELISA Reader. This screening led to a selection of antibodies binding well to Cynomolgus IgG as well as exhibiting no/a low cross reactivity to human IgG. This selection of antibodies was further subjected to assay b).

b) Selection of Antibodies without Detectable Cross Reactivity to Human IgG

In order to identify, from the selection of antibodies of the primary screening a), those that exhibit no detectable cross reactivity to human IgG, the assay described in the following was performed. MTPs pre-coated with recombinant Streptavidin (MicroCoat, Bernried, lot MC 1098) were coated with biotinylated Cynomolgus IgG, 250 ng/mL, in PBS (phosphate buffered saline) with 1.0% BSA II (100 μL per well, 60 min. incubation at ambient temperature, with shaking), and subsequently washed 3 times with 0.9% (w/v) NaCl/ 0.05% Tween® 20. In the next step per well 100 μL of the antibody solution to be assayed (culture supernatant), and 50 μL of PBS (reference signal), or 50 μL of a solution of human IgG (80 mg/mL; final concentration in the assay: 27 mg/mL; assay signal), respectively, were added, and incubated for 60 min. at ambient temperature, with shaking. After three wash steps with 0.9% (w/v) NaCl/0.05% Tween® 20 per well, 100 μL of a horseradish peroxidase-labeled F(ab')$_2$ fragment of a polyclonal sheep anti-mouse Fcγ antibody were added for the detection of bound sample antibody, and incubated for 60 min. at ambient temperature, with shaking. Subsequently, washing was performed as above. Finally, per well 100 μL of ABTS® (Roche Diagnostics GmbH, catalog no. 1684302) were added. After 30 min. incubation at ambient temperature, the extinction was measured at [405/492] nm in a commercial microtiter plate ELISA Reader. Antibodies exhibiting an assay signal not significantly differing from the associated reference signal were selected for further use. In quantitative terms, this equals an estimated cross reactivity to Human IgG of <0.001%.

(Definition of "not significantly differing": Assay signal=90-110% of reference signal.)

Example 4

Preparation of a Conjugate of Cynomolgus IgG (Cyno-IgG) with Human IgG (H-IgG)

a) Preparation of Cyno-IgG-SATP

Cynomolgus IgG purified from cynomolgus serum by ion exchange chromatography and gel filtration has been dialyzed against 30 mM potassium phosphate buffer, pH 7.1, and the resulting protein solution was adjusted to a protein concentration of about 10 mg/ml. N-succinimidyl-3-acetyl-thiopropionate (SATP) was dissolved in DMSO and added to the antibody solution in a molar ratio of 1:5 (IgG:SATP). The mixture was incubated for 60 min. at 25° C. at pH 7.1. The reaction was stopped by adding L-lysine at a final concentration of 10 mM, the pH was adjusted to pH 6.1, and the surplus of SATP was removed by dialysis against 10 mM potassium phosphate buffer, with 200 mM NaCl and 1 mM EDTA, pH 6.1.

b) Preparation of H-IgG-MH

Human IgG purified from human serum by ion exchange chromatography was dialyzed against 30 mM potassium phosphate buffer, pH 7.1, and the resulting protein solution was adjusted to a protein concentration of about 20 mg/ml. Maleimidohexanoyl-N-hydroxysuccinimide ester (MHS) was dissolved in DMSO and added to the antibody solution in a molar ratio of 1:6 (IgG:MHS). The mixture was incubated for 60 min. at 25° C. at pH 7.1. The reaction was stopped by adding L-lysine to a final concentration of 10 mM, the pH was adjusted to 6.1, and the surplus of MHS was removed by dialysis against 10 mM potassium phosphate buffer, with 200 mM NaCl and 1 mM EDTA, pH 6.1.

c) Conjugation of Cyno-IgG-SATP with H-IgG-MH

Cyno-IgG-SATP was deacetylated to Cyno-IgG-SH by adding 2.5% (v/v) 1 M hydroxylamine solution, pH 7.5, and incubating for 60 min. at 25° C. The deacetylated antibody was mixed with H-IgG-MH (molar ratio of Cyno-IgG-SH:H-IgG-MH=1:1) to a final concentration of about 7 mg/ml of total IgG. The pH was adjusted to 7.1 and the mixture was incubated at 25° C. The conjugation process was analyzed with an analytical gel filtration column (e.g. TSK 3000). The conjugation process was stopped after 40 min. in general, by adding cysteine to a final concentration of 2 mM. After 30 min. incubation time N-methylmaleimide (NMM) was added to a final concentration of 5 mM and the pH was adjusted to 7.5. After 60 min. incubation at 25° C. the conjugate was separated by gel filtration chromatography with Sephacryl S-300 to remove non-conjugated antibodies.

Example 5

Preparation of Digoxigenylated Monoclonal Anti-Cynomolgus-Fc Antibody a) Preparation of Monoclonal Anti-Cynomolgus-Fc Antibody The fermentation supernatant of monoclonal anti-Cynomolgus-Fc antibody was concentrated about tenfold, transferred to a buffer with 20 mM TRIS, 1 M ammonium sulfate, pH 9.0, and applied to Protein A-sepharose. The eluate with 0.2 M sodium citrate at pH 3.0 was dialyzed against phosphate buffer, pH 7.5. Contaminants of bovine IgG (from FCS in the fermentation broth) were separated by immunoadsorption with immobilized antibodies against bovine IgG.

b) Digoxigenylation of Monoclonal Anti-Cynomolgus-Fc Antibody

A solution of the monoclonal anti-Cynomolgus-Fc antibody in phosphate buffer was adjusted to pH 8.1 and to a concentration of about 2 mg/ml. Digoxigenin-3-O-methyl-carbonyl-ε-aminocaproic acid-N-hydroxysuccinimide ester was dissolved in DMSO and added to the antibody solution in a molar ratio of 1:5. The reaction was stopped after 60 min. by adding L-lysine, and the surplus of the labeling reagent was removed by dialysis against 50 mM potassium phosphate buffer, with 150 mM NaCl, pH 7.5.

Example 6

Assessment of Antibody Binding/Specificity by the BIAcore® System

All measurements were performed with the BIAcore®2000 instrument using a CM5-chip. Coating this chip with an antibody was achieved by standard amine coupling. Unless otherwise indicated all incubations were performed in HBS-buffer (HEPES, NaCl, pH 7.4) at 25° C. A saturating amount of different monoclonal anti-Cynomolgus-IgG antibody, MAB M-R10Z8E9, and polyclonal anti-human Fcγ antibody (Dianova, Germany), respectively, was immobilized by amine coupling on different channels of the same CM5-chip. All animal sera were diluted in HBS buffer containing 1 mg/ml CM-dextran at a final concentration of 1%. Binding was analyzed by injection of the 1 in 100 diluted sera and incubation for 60 seconds. Dissociation was measured by washing the chip surface with HBS buffer for 180 seconds. Using BIAevaluation Software from BIAcore® the dissociation constant values (=KDiss.) were calculated with a 1:1 Langmuir fitting model. For all animal sera this calculation was based on the assumption that the IgG level is 15 mg/ml. The signal values 80 seconds after start of the injection of the test antibody were chosen for the comparison of the amount of IgG bound (RU in Table 2).

TABLE 2

Binding signals [RU] of animal sera to monoclonal
anti-Cynomolgus-IgG antibody and a
polyclonal anti-Human-Fcγ antiserum

| Sample (Serum) | Anti-Cynomolgus mAb (clone 3.25.12) | | PAb<H-Fcγ> | |
|---|---|---|---|---|
| | Bound RU | KDiss. in mol/L | Bound RU | KDiss. in mol/L |
| Marmoset | −31.4 | no binding | 532 | $1.41 * 10^{-08}$ |
| Baboon | 2038.5 | $9.39*10^{-13}$ | 1404.6 | $6.37 * 10^{-11}$ |
| Rat | −20.9 | no binding | 48.2 | no binding |
| Chimpanzee | −28.2 | no binding | 1918.1 | $3.72 * 10^{-13}$ |
| Cynomolgus | 2278.7 | $2.03 * 10^{-09}$ | 1344.8 | $7.17 * 10^{-12}$ |
| Rhesus Macaque | 2362.8 | $5.09 * 10^{-10}$ | 1172.1 | $9.08 * 10^{-11}$ |
| NMRI-Mouse | −15.7 | no binding | −23.8 | no binding |
| Human | −25.5 | no binding | 1571.6 | $4.56 * 10^{-12}$ |
| Dog | −35.9 | no binding | 564.3 | $1.15 * 10^{-08}$ |
| CD1-Mouse | −40.4 | no binding | −30.7 | no binding |

Table 2 shows that the monoclonal anti-Cynomolgus-IgG antibody does not cross-react with Human serum. Only the IgG comprised in Cynomolgus, Rhesus, and Baboon serum is detected. In contrast to the monoclonal anti-Cynomolgus-IgG antibody shows the polyclonal anti-Human Fc antibody a high reactivity with sera of human, dog, and all tested monkey species.

Example 7

Assay for DA/ADA Complex without Adding DA

Figure 1:
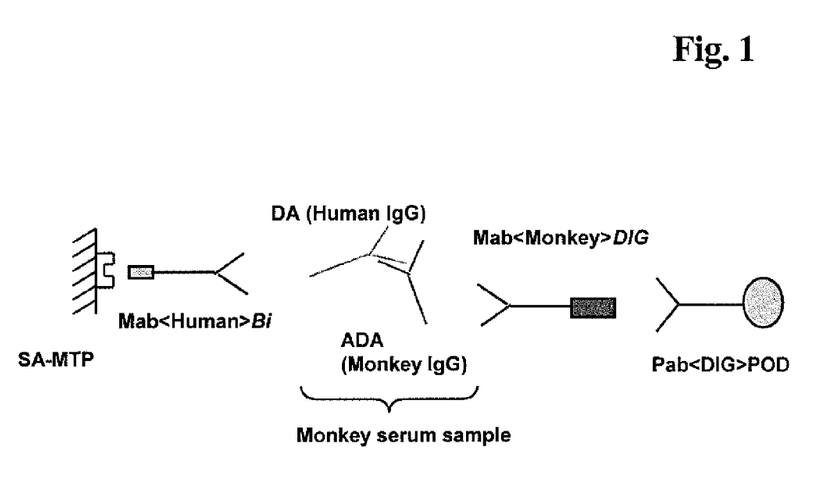

Biotinylated MAB M-R10Z8E9 was bound to the wells of a Streptavidin-coated microtiter plate (SA-MTP) in the first step. Excess of unbound antibody was removed by washing. Afterwards the monkey serum samples and the reference standards (Human IgG chemically conjugated with Cynomolgus IgG spiked in 1% Cynomolgus serum) were incubated in the wells. After washing away unbound substances the bound DA/ADA complex was detected with digoxigenylated anti-Cynomolgus antibodies followed by incubation with a horse-radish peroxidase labeled anti-digoxigenin antibody. The antibody-enzyme conjugate catalyzes the color reaction of the ABTS® substrate. The signal was measured by ELISA reader at 405 nm wavelength (reference wavelength: 490 nm ([405/490] nm)). Absorbance values of each serum sample were determined in duplicates. A scheme exemplifying this test system is shown in FIG. 1.

Example 8

Assay for DA/ADA Complex—with Adding DA

Figure 2:
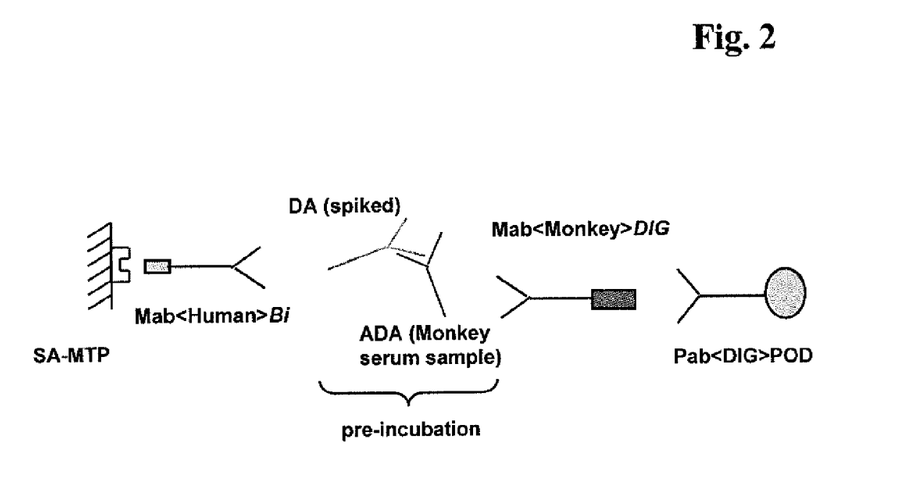

Before sample analysis monkey serum samples were diluted in PBS-based buffer and spiked with drug antibody. After 15 min. preincubation the samples were analyzed with above-mentioned ELISA. A scheme exemplifying this test system is shown in FIG. 2.

Example 9

Detection of DA/ADA Complexes in Samples of a Cynomolgus PK-Study

Figure 5:
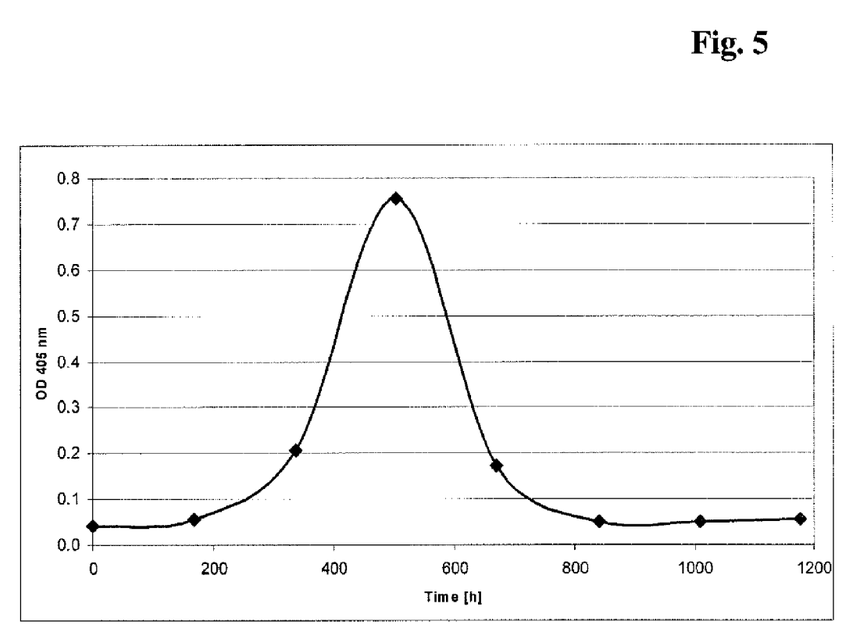
FIG. 5: Detection of DA/ADA complexes in samples of a Cynomolgus Single Dose PK study of HuMab<IGF-1R> (3 mg/kg; iv).
At 8 time points between 0 h and 1176 h after drug dosing serum samples were collected and analyzed with the ELISA (shown in FIG. 1) without adding drug antibody. The amount of DA/ADA complexes (OD signal at 405 nm) is plotted vs. time after dosing.
Figure 6:
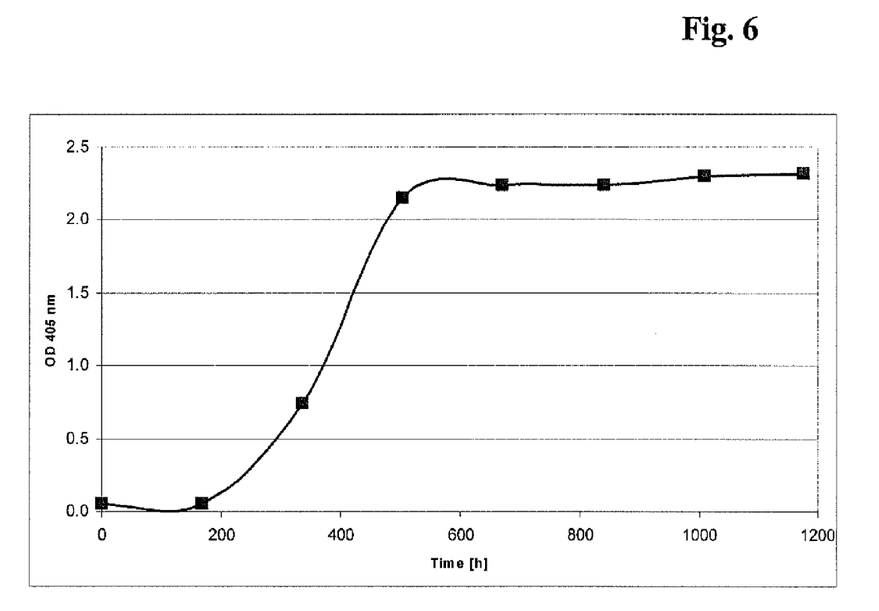
FIG. 6: Detection of DA/ADA complexes in samples of a Cynomolgus Single Dose PK study of HuMab<IGF-1R> (3 mg/kg; iv).
At 8 time points between 0 h and 1176 h after drug dosing serum samples were collected and analyzed with the ELISA (shown in FIG. 2) with adding drug antibody. The amount of DA/ADA complexes (OD signal at 405 nm) is plotted vs. time after dosing.
Figure 7:
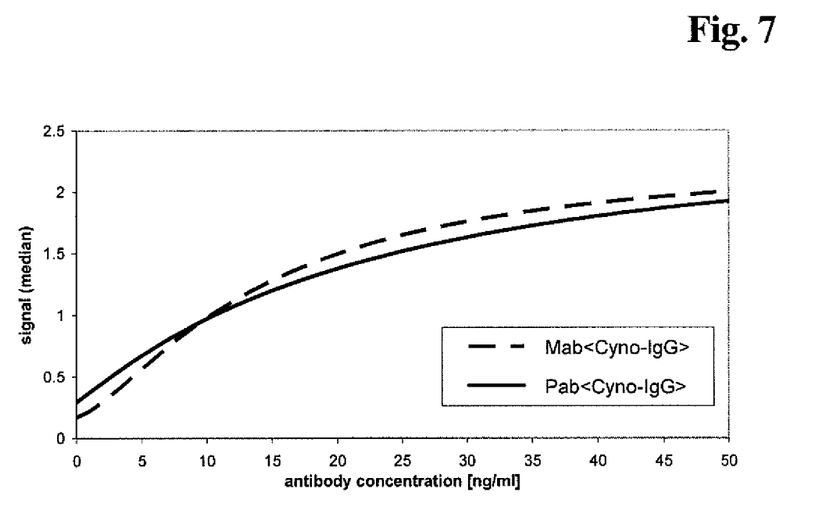
FIG. 7: Comparison of the detection of Cynomolgus IgG by a monoclonal anti-Cynomolgus IgG and a polyclonal-Cynomolgus IgG
The optical densities (signal (median)) are given for various concentrations of human IgG chemically conjugated to Cynomolgus IgG diluted in PBS-based-buffer with 1% (v/v) Cynomolgus serum

Serum samples of a Cynomolgus Single Dose PK-study (PK=pharmacokinetic) with a human antibody against IGF-1R (WO 2005/005635; 3 mg/kg; iv) were analyzed with above mentioned ELISA: i) detection of DA/ADA complexes without adding drug antibody (FIG. 5), and ii) detection of DA/ADA complexes with adding drug antibody (FIG. 6). At 8 time points between 0 h and 1176 h after dosing serum samples were collected and analyzed. The amount of DA/ADA complexes (OD signal at 405 nm) was plotted vs. time after dosing in a diagram. As FIG. 5 shows, positive signals without in vitro adding of drug antibody were only detected in serum samples between 336 h and 672 h (peak shape) if AD/ADA complexes formed in vivo. In absence of anti-drug antibodies no immune complexes were formed and no positive signals were detected (time points before 336 h). Due to the absence of drug in samples 672 h after dosing or later no complexes were detectable. With adding drug antibody to the serum sample as preincubation step both in vivo formed and in vitro formed DA/ADA complexes were detected/are detectable. A positive signal only depends on the generation of ADA as demonstrated in FIG. 6. Both diagrams (FIGS. 5 and 6) correlate well with the drug-time curve.

Example 10

Assay for ADA-Detection Using Anti-Cynomolgus Antibodies

Figure 3:
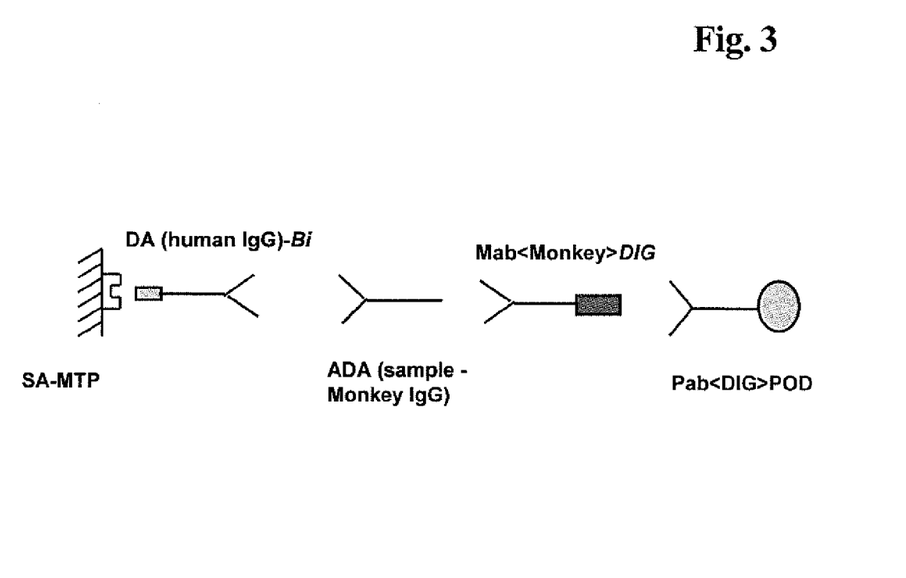
Figure 4:
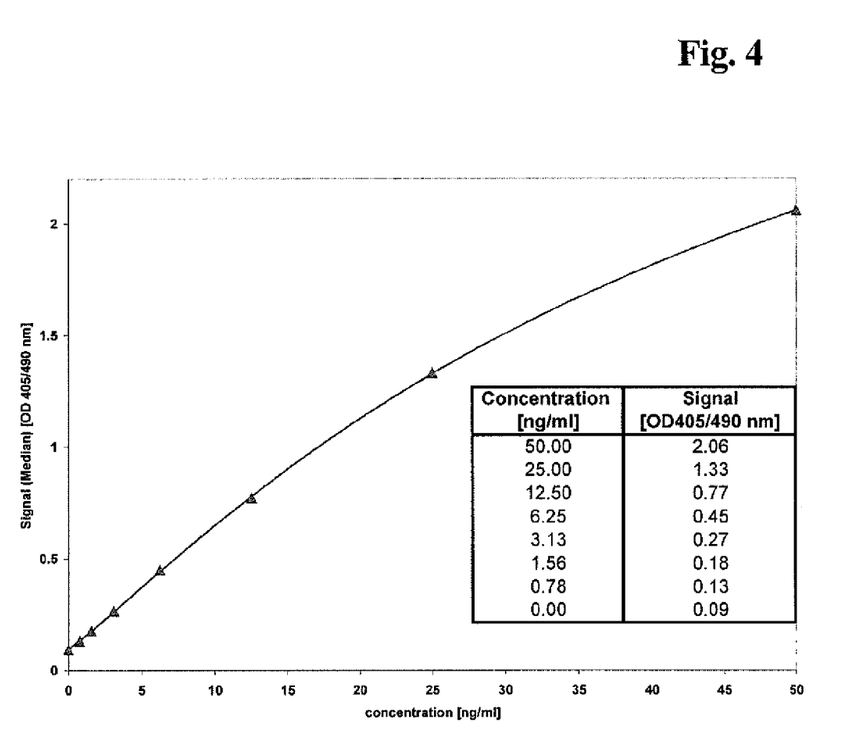

Biotinylated drug antibody (human antibody against IGF-1R) was bound to the wells of a Streptavidin-coated microtiter plate (SA-MTP) in the first step. The excess of unbound antibody was removed by washing. Afterwards the monkey serum samples (20-fold diluted in PBS-based buffer) and the reference standards were incubated. After washing away unbound substances the bound anti-drug antibody (ADA) was detected with digoxigenylated anti-Cynomolgus antibody followed by incubation with a horse-radish peroxidase labeled anti-digoxigenin antibody. The antibody-enzyme conjugate catalyzes the color reaction of the ABTS® substrate. The signal was measured by ELISA reader at 405 nm wavelength (reference wavelength: 490 nm). Absorbance values of each serum sample were determined in triplicates. A scheme exemplifying this test system is shown in FIG. 3.

Example 11

Preparation of Polyclonal Antibodies Against Cynomolgus IgG a) Purification of Polyclonal Antibodies from Rabbit Serum Rabbits have been immunized with Cynomolgus Fc according to standard methods. In the raw serum of five rabbits immunized with Cynomolgus Fc the lipid components were removed by delipidation with Aerosil (1.5% (w/v)) and the immunoglobulins were precipitated with ammonium sulphate (1.7 M). After acid treatment (30 min., at pH 5.5) and dialysis against 15 mM potassium phosphate buffer, supplemented with 50 mM NaCl, pH 7.0, the mixture was separated by DEAE ion exchange chromatography at pH 7.0 and the IgG fraction in the flow through (=rabbit polyclonal anti-Cynomolgus-IgG antibody) was concentrated to about 25 mg/ml.

b) Preparation of Affinity Purified Polyclonal Rabbit Anti-Cynomolgus IgG Antibodies (pAb<Cyno-IgG>) without Cross-Reactivity Against Human IgG The concentrated IgG fraction of step a) was transferred to a buffer system with 50 mM potassium phosphate, supplemented with 150 mM NaCl, pH 7.5 (PBS). The immunosorbent with immobilized Cynomolgus-IgG, prepared by conjugation of Cynomolgus-IgG to NHS-sepharose by state of the art techniques, was packed into a column and equilibrated with 50 mM potassium phosphate buffer, supplemented with 150 mM NaCl pH 7.5.

10 mg IgG/ml immunosorbent were applied to the column equilibrated with PBS. The column was washed successively with PBS, 0.5 M NaCl supplemented with 0.05% (w/v) Tween® 20, and 30 mM NaCl. The IgG specifically bound to the affinity matrix was eluted with 3 mM HCl and 1 M propionic acid and dialyzed against PBS.

To eliminate the antibodies with cross reactivity against human IgG the affinity-purified antibodies were applied to an affinity column with immobilized human IgG, prepared by conjugation of unspecific human IgG to NHS-sepharose by state of the art techniques. The column was equilibrated with PBS. About 6 mg IgG/ml immunosorbent were applied to the column. The specific polyclonal IgG-fraction is in the flow through. After regeneration of the column with 0.5 M NaCl supplemented with 0.05% (w/v) Tween® 20, 30 mM NaCl, 1 M propionic acid, and PBS. The immunosorption of unspecifically binding IgG was repeated two times to completely eliminate antibodies with cross reactivity against human IgG.

The resulting purified polyclonal anti-Cynomolgus-IgG antibody without cross reactivity to human IgG was concentrated to about 4 mg/ml and stored at −80° C.

Example 12

Assessment of Antibody Binding/Specificity of the Polyclonal Rabbit Anti-Cynomolgus Pc Antibodies (pAb<Cyno-Fc>) by the BIAcore® System All measurements were performed with the BIAcore® 2000 instrument using a CM5-chip. Coating this chip with an antibody was achieved by standard amine coupling. Unless otherwise indicated all incubations were performed in HBS-buffer (HEPES, NaCl, pH 7.4) at 25° C. A saturating amount of the polyclonal anti-Cynomolgus-IgG antibody was immobilized by amine coupling on the CM5-chip. All animal sera were diluted in HBS buffer containing 1 mg/ml CM-dextran at a final concentration of 1%. Binding was analyzed by injection of the 1 in 100 diluted sera and incubation for 60 seconds. Dissociation was measured by washing the chip surface with HBS buffer for 180 seconds. Using BIAevaluation Software from BIAcore® the dissociation constant values (=KDiss.) were calculated with a 1:1 Langmuir fitting model. For all animal sera this calculation was based on the assumption that the IgG level is 15 mg/ml. The signal values 80 seconds after start of the injection of the test antibody were chosen for the comparison of the amount of IgG bound (RU in Table 3).

TABLE 3

Binding signals [RU] of animal sera to polyclonal anti-Cynomolgus-IgG antibody

| | Anti-Cynomolgus pAb | |
|---|---|---|
| Sample (Serum) | Bound RU | KDiss. in mol/L |
| Marmoset | 50.8 | $1.80 * 10^{-07}$ |
| Baboon | 1297.4 | $4.11 * 10^{-10}$ |
| Rat | −12.4 | no binding |
| Chimpanzee | 3.8 | no binding |
| Cynomolgus | 1357.9 | $1.92 * 10^{-09}$ |
| Rhesus Macaque | 1244.6 | $2.16 * 10^{-09}$ |
| NMRI-Mouse | 42.1 | $4.27 * 10^{-06}$ |
| Human | −6.7 | no binding |
| Dog | −10 | no binding |
| CD1-Mouse | −15.9 | no binding |

Table 3 shows that polyclonal anti-Cynomolgus-IgG antibody does not cross-react with Human serum. Only the monkey IgG comprised in Marmoset, Cynomolgus, Rhesus, and Baboon serum is detected. In contrast to monoclonal anti-Cynomolgus-IgG antibody shows the polyclonal anti-Cynomolgus IgG antibody a reactivity with the serum of NMRI-mouse. Also the polyclonal anti-Cynomolgus IgG antibody is not binding to human IgG and has at least a 100-fold reactivity difference between the reactivity to monkey IgG and mouse IgG.

The invention claimed is:

1. A monoclonal antibody that binds to Cynomolgus IgG and does not bind to human IgG, wherein the monoclonal antibody is produced by a hybridoma cell line deposited with the Deutsche Sammlung von Microorganismen und Zellkulturen GmbH under Accession Nos. DSM ACC 2799, DSM ACC 2800, DSM ACC 2801, DSM ACC 2802 or DSM ACC 2803.

2. A hybridoma cell line producing a monoclonal antibody that binds to Cynomolgus IgG and does not bind to human IgG, wherein the hybridoma cell line is deposited with the Deutsche Sammlung von Microorganismen und Zellkulturen GmbH under Accession Nos. DSM ACC 2799, DSM ACC 2800, DSM ACC 2801, DSM ACC 2802 or DSM ACC 2803.

3. A composition comprising at least two monoclonal antibodies, wherein the at least two monoclonal antibodies are produced by two or more hybridoma cell lines selected from the group consisting of DSM ACC 2799, DSM ACC 2800, DSM ACC 2801, DSM ACC 2802 and DSM ACC 2803.

4. A method for the immunological determination of an immune complex (DA/ADA complex) of a drug antibody (DA) and an antibody against the drug antibody (ADA) in a monkey species sample using a double antigen bridging assay, the method comprising:
incubating the sample with a capture antibody and a tracer antibody;
wherein one of the capture or tracer antibody is a monoclonal antibody that binds to Cynomolgus IgG, does not bind to human IgG, and is produced by a hybridoma cell line selected from the group consisting of DSM ACC 2799, DSM ACC 2800, DSM ACC 2801, DSM ACC 2802 and DSM ACC 2803; and wherein the other of the capture or tracer antibody is an antibody that binds to human IgG; and
detecting formation of a sandwich complex of capture antibody, DA/ADA complex, and tracer antibody; wherein the amount of sandwich complex formed is correlated to the concentration of and DA/ADA complex in the sample.

5. The method of claim 4, wherein the monkey species sample is preincubated with a predetermined amount of the drug antibody.

* * * * *